United States Patent
Doerr

(10) Patent No.: US 8,255,063 B2
(45) Date of Patent: Aug. 28, 2012

(54) INTRACARDIAL ELECTRODE LINE AND CARDIAC STIMULATOR

(75) Inventor: Thomas Doerr, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 690 days.

(21) Appl. No.: 12/268,946

(22) Filed: Nov. 11, 2008

(65) Prior Publication Data
US 2009/0138060 A1    May 28, 2009

(30) Foreign Application Priority Data

Nov. 28, 2007 (DE) .......................... 10 2007 057 227

(51) Int. Cl.
*A61N 1/368* (2006.01)
(52) U.S. Cl. .............. 607/119; 607/1; 607/2; 607/5; 607/9; 607/17; 607/32; 607/60; 607/115; 607/116; 607/122; 607/123; 600/508; 600/509; 600/513; 600/523
(58) Field of Classification Search .............. 607/1–2, 607/4, 9, 17, 25, 32, 60, 115–116, 119, 122, 607/123; 600/508–509, 513, 523
See application file for complete search history.

(56) References Cited

U.S. PATENT DOCUMENTS

| | | | |
|---|---|---|---|
| 5,628,777 A | | 5/1997 | Moberg et al. |
| 7,024,244 B2 * | | 4/2006 | Muhlenberg et al. ........... 607/23 |
| 2003/0105496 A1 | | 6/2003 | Yu et al. |
| 2004/0172078 A1 | | 9/2004 | Chinchoy |
| 2004/0172079 A1 | | 9/2004 | Chinchoy |
| 2005/0027320 A1 | | 2/2005 | Nehls |
| 2005/0137671 A1 | | 6/2005 | Liu et al. |
| 2006/0178586 A1 * | | 8/2006 | Dobak, III .................... 600/508 |
| 2008/0039904 A1 * | | 2/2008 | Bulkes et al. .................. 607/62 |

FOREIGN PATENT DOCUMENTS

| | | |
|---|---|---|
| EP | 0727242 | 8/1996 |
| WO | 9913940 | 3/1999 |
| WO | 2006086435 | 8/2006 |
| WO | 2006113659 | 10/2006 |

OTHER PUBLICATIONS

European Search Report, dated Apr. 1, 2009, 7 pages.
Richards et al., "An Implantable Intracardiac Accelerometer for Monitoring Myocardial Contractility", Pacing and Clinical Electrophysiology 19 (12), pp. 2066-2071.

* cited by examiner

*Primary Examiner* — Carl H Layno
*Assistant Examiner* — Deborah Malamud
(74) *Attorney, Agent, or Firm* — ARC IP Law, PC; Joseph J. Mayo

(57) ABSTRACT

The invention relates to an intracardial implantable electrode line for connection to an implantable medical device, in particular a cardiac pacemaker or cardioverter/defibrillator or the like, which has an acceleration sensor in the area of its distal end, which is implemented to record and differentiate acceleration values in at least two different directions. The invention additionally relates to a cardiac stimulation configuration which also has a cardiac stimulator in addition to such an electrode line.

11 Claims, 6 Drawing Sheets

INTRACARDIAL ELECTRODE LINE AND CARDIAC STIMULATOR

Figure 1:
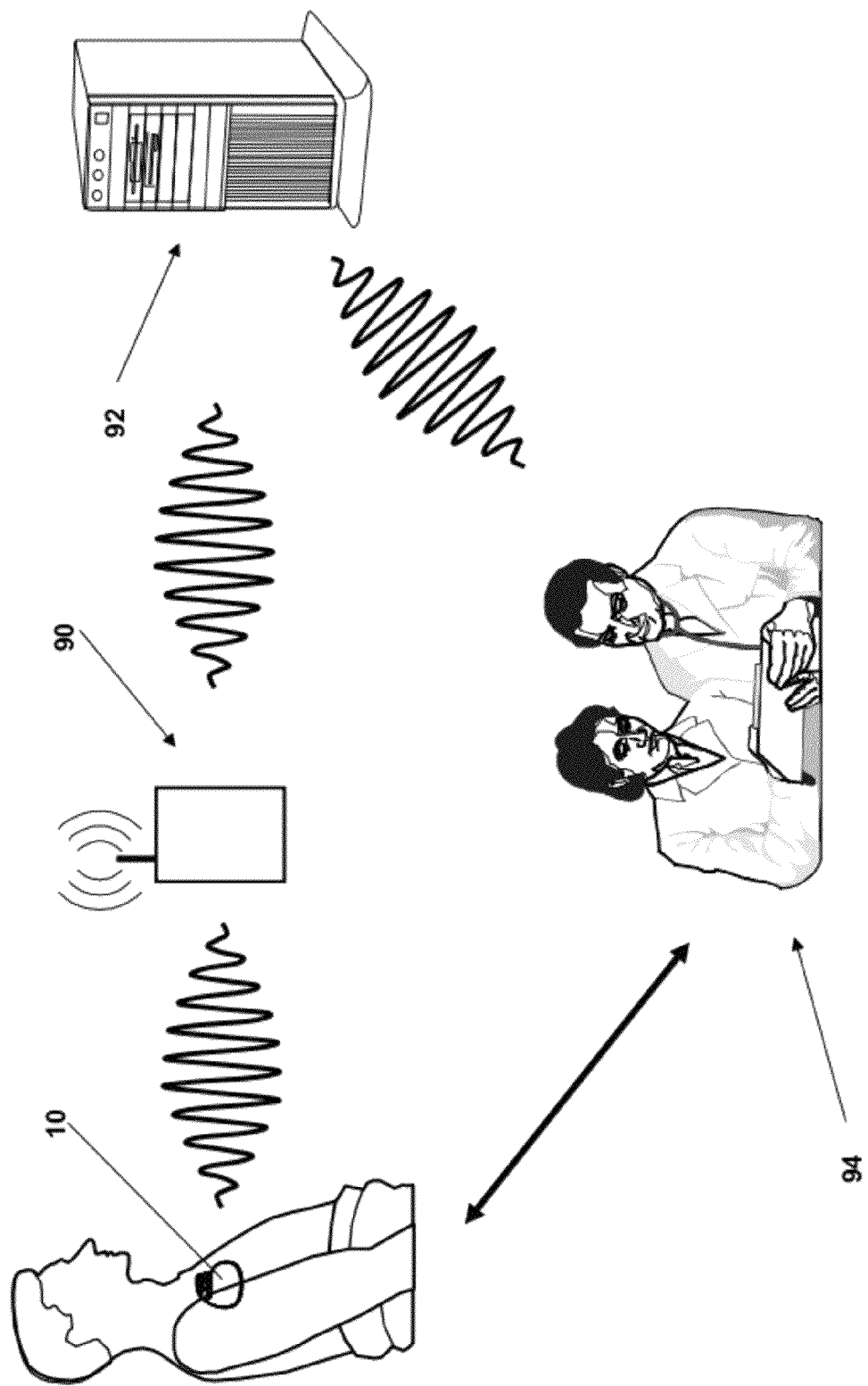

This application takes priority from German Patent Application DE 10 2007 057 227.3, filed 28 Nov. 2007, the specification of which is hereby incorporated herein by reference.

BACKGROUND OF THE INVENTION

1. Field of the Invention

The invention relates to an electrode line for an implantable cardiac stimulator for delivering electrical stimulation pulses for therapy of a heart, e.g., cardial resynchronization therapy (CRT) of a heart, as well as such a cardiac stimulator itself. The cardiac stimulator may be a cardiac pacemaker or an implantable cardioverter/defibrillator (ICD) or a combination of both, which is capable of stimulating both ventricles of a heart.

2. Description of the Related Art

A cardiac stimulator of this type typically has at least one right-ventricular sensing unit and one right-ventricular stimulation unit as well as one left-ventricular sensing unit and one left-ventricular stimulation unit. These units are each connected in operation of the cardiac stimulator via electrode lines to electrodes to be implanted at suitable points in the heart. The electrode line having the electrodes for detecting electrical potentials in the left ventricle of the heart and for delivering left-ventricular stimulation pulses are typically a component of a left-ventricular electrode line, which is laid through the coronary sinus of a heart and is therefore also referred to as a coronary sinus electrode line. The electrodes for detecting electrical potentials in the right ventricle and for delivering right-ventricular stimulation pulses are typically fastened to a right-ventricular electrode line whose distal end extends up into the apex of the right ventricle. The electrode lines are typically connected at their proximal end via standardized plug connections to a corresponding cardiac stimulator.

The typical stimulation modes of a right-ventricular cardiac stimulator, such as VVI, VVD, or DDD, may be presumed to be known. This is also true for the delivery of stimulation pulses only in case of demand (demand pacemaker), in which the delivery of a stimulation pulse to a particular chamber of a heart is suppressed if a particular intrinsic action (intrinsic contraction) of the particular ventricle was previously detected in a corresponding escape interval via a sensing unit of the cardiac stimulator assigned to this ventricle. These concepts, which are known per se, may also be implemented in the cardiac stimulator described here.

The cardiac stimulator discussed here is preferably a biventricular cardiac stimulator which is fundamentally capable of stimulating both ventricles of the heart continuously or on demand.

In particular for cardiac stimulators of this type, the need exists to adapt the particular therapy as well as possible to the particular hemodynamic status of the patient.

Currently, various methods for detecting the hemodynamics are being researched. Either direct methods of pressure measurement in the pulmonary vein, left atrium, or ventricle are studied here, or indirect methods of impedance cardiography are being pursued. The methods of pressure measurement have the disadvantage that additional sensors are implanted in the heart. These sensors require an increased effort during implantation, because the desired implantation locations differ from the standard electrodes (ICD and pacemaker).

The impedance-based methods have the disadvantage that the hemodynamic variables may only be derived indirectly here and thus the disadvantage of replicability exists. The question always arises as to whether the physician believes in these methods.

Integrating an acceleration sensor (accelerometer) in intracardial electrode line, which provides information about the movement of the electrode line, which correlates to a certain degree with the movement of a particular heart part, see, for example, US 2004/0172078, US 2004/0172079, and US 2005/0027320, has already been suggested. Furthermore, in "An Implantable Intracardiac Accelerometer for Monitoring Myocardial Contractility", Pacing and Clinical Electrophysiology 19 (12), pages 2066-2071, a direction-independent application of an accelerometer integrated in the electrode has been described. In spite of the results, which were already published in 1996, up to this point there has been no successful commercial usage of the concept.

BRIEF SUMMARY OF THE INVENTION

The object of the invention is to detect information for an electronic implant about the hemodynamic status and its changes in a significantly improved way, which is more strongly correlated than already known methods. The invention is preferably also to solve the problem that the methods known up to this point were not able to be replicated by the user in their action and therefore were frequently rejected.

The inventor has come to the finding that without directional information in regard to detected acceleration values, a correlation of the perceived wall movement to the accelerometer signal (output signal of the acceleration sensor/accelerometer) is only possible in a restricted way.

Based on this finding, the achievement of the above-mentioned object comprises an electrode line having a proximal end which is implemented to connect the electrode line to an implantable medical device, in particular a cardiac pacemaker or cardioverter/defibrillator or the like, as well as a distal end, which carries at least one electrode for delivering stimulation pulses or for recording intracardial electrical signals, as well as an acceleration sensor, the acceleration sensor being implemented to record acceleration values in at least two different directions and thus being able to detect direction-dependent acceleration values and output corresponding accelerometer output signals.

On the basis of the directional dependency of the detected acceleration values, a specific imaging of a wall movement of a heart wall and its reliable correlation to the cardiac output are provided.

The electrode line preferably has a plug contact on its proximal end and an electrical line (e.g., in the form of an electrically conductive wire), which electrically connects a contact surface of the plug contact to the electrode. The acceleration sensor is connected to a modulator, and the modulator is in turn connected to the electrical line, the modulator being implemented to give an output signal of the acceleration sensor to the electrical line in modulated form. In this way, the accelerometer output signals may be transmitted wire-bound from the acceleration sensor to a cardiac stimulator, which is possibly connected to the electrode line, without having to provide further electrical lines in the electrode line.

Alternatively thereto, the acceleration sensor may also be connected to a transmitter for the wireless transmission of the output signals of the acceleration sensor.

Using an electrode line of this type, a cardiac stimulation configuration having a cardiac stimulator connected to the electrode line may be provided, which information based on the actual mechanical dynamics of the heart muscle having direct correlation to the hemodynamics, which may be used directly as a diagnostic variable or as a control variable for the therapy control of the electronic implant. The implantation procedure is not changed by this additional sensor due to the integration of the sensor in an electrode to be implemented in any case. Furthermore, altered terminal technology for the existing implants is not necessary if the sensor is integrated in a bipolar probe (IS-1 standard).

The electrode line is preferably implemented as a left-ventricular electrode line for implantation through the coronary sinus and is used for stimulation of the left ventricle of a heart.

The invention presented here comprises the integration of a direction-dependent acceleration sensor in an intracardial electrode line, the left-ventricular electrode line (e.g., CS electrode line) therefore being preferred, because the left-ventricular dynamics correspond to the greatest correlation with the overall hemodynamics. The integrated acceleration sensor also delivers the direction of the acceleration in at least 2 vectors in addition to the acceleration information.

The cardiac stimulator or implantable monitor connected to this electrode line operation is, in addition to the normal intracardial electrogram signals, additionally to analyze the accelerometer output signal of the direction-dependent acceleration sensor integrated in the electrode and provide it to an analysis and control unit at least as diagnostic information or also as a control signal for the therapy of the electronic implant To allow a simple correlation of the accelerometer output signals to the hemodynamics of the patient in connection with the echocardiography, according to a preferred embodiment variant, the electrode line has at least one radioopaque or echogenic section in the area of its distal end, which is well recognizable using imaging methods such as computer tomography or also echocardiography. By additionally introducing echogenic structures into the electrode line, their visibility in echocardiography results, so that the signals of the acceleration sensor may be correlated with the hemodynamic findings obtained from stress/echocardiography.

A cardiac stimulation configuration having a left-ventricular electrode line of the previously described type and an implantable cardiac stimulator, to which the left-ventricular electrode line and a right-ventricular electrode line are connected, is especially preferred. The right-ventricular electrode line also carries a right-ventricular acceleration sensor, which is implemented to record acceleration values in at least two different directions, in the area of its distal end in this case.

With a configuration of this type having two electrode lines having acceleration sensors on their distal ends, the direction-related acceleration information ensures a reliable distance measurement of two implanted probes. Without the direction information, opposing movements could not be differentiated from movements in the same direction. The accelerometer output signals of the two acceleration sensor situated in the different electrode lines primarily allow the distance change of the distal ends of the electrode lines to be calculated from the detected acceleration values. This is sufficient to detect short-term changes of the hemodynamics. For a long-term analysis, a calibration of this system may additionally be performed with the aid of echocardiography, for example. A comparison to reference curves (see also below), which were recorded at defined phases (e.g., at rest) may also be performed.

The right-ventricular electrode line also has a plug contact on its proximal end and an electrical line which electrically connects a contact surface of the plug contact to an electrode in the area of the distal end of the right-ventricular electrode line. The right-ventricular acceleration sensor is preferably also connected to a modulator, which is in turn connected to the electrical lines provided in any case, so that no additional lines are necessary. This is possible because the modulator gives a particular accelerometer output signal of the acceleration sensor in modulated form to the electrical line, so that it is to be transmitted in addition to possible stimulation pulses via the same line (or the same line pair).

Instead of the modulator or in addition thereto, a transmitter for the wireless transmission of the output signals of the acceleration sensor may also be connected to the right-ventricular acceleration sensor.

A further acceleration sensor is preferably integrated in a housing of the cardiac stimulator. A compensation of the superimposed movement of the patient may then be performed via analysis of the accelerometer output signals of the acceleration sensor additionally integrated in the housing of the cardiac stimulator.

The cardiac stimulator additionally preferably has an analysis unit which is connected or is to be connected at least indirectly to the acceleration sensor and which is implemented to analyze a particular accelerometer output signal by a comparison to reference curves stored in the cardiac stimulator, the stored reference curves having been obtained under defined conditions, e.g., at rest or by the physician in the context of an echocardiography examination.

Further advantageous embodiments result by combination of the features described here with one another and with those features which are known from the prior art.

BRIEF SUMMARY OF THE INVENTION

Figure 2:
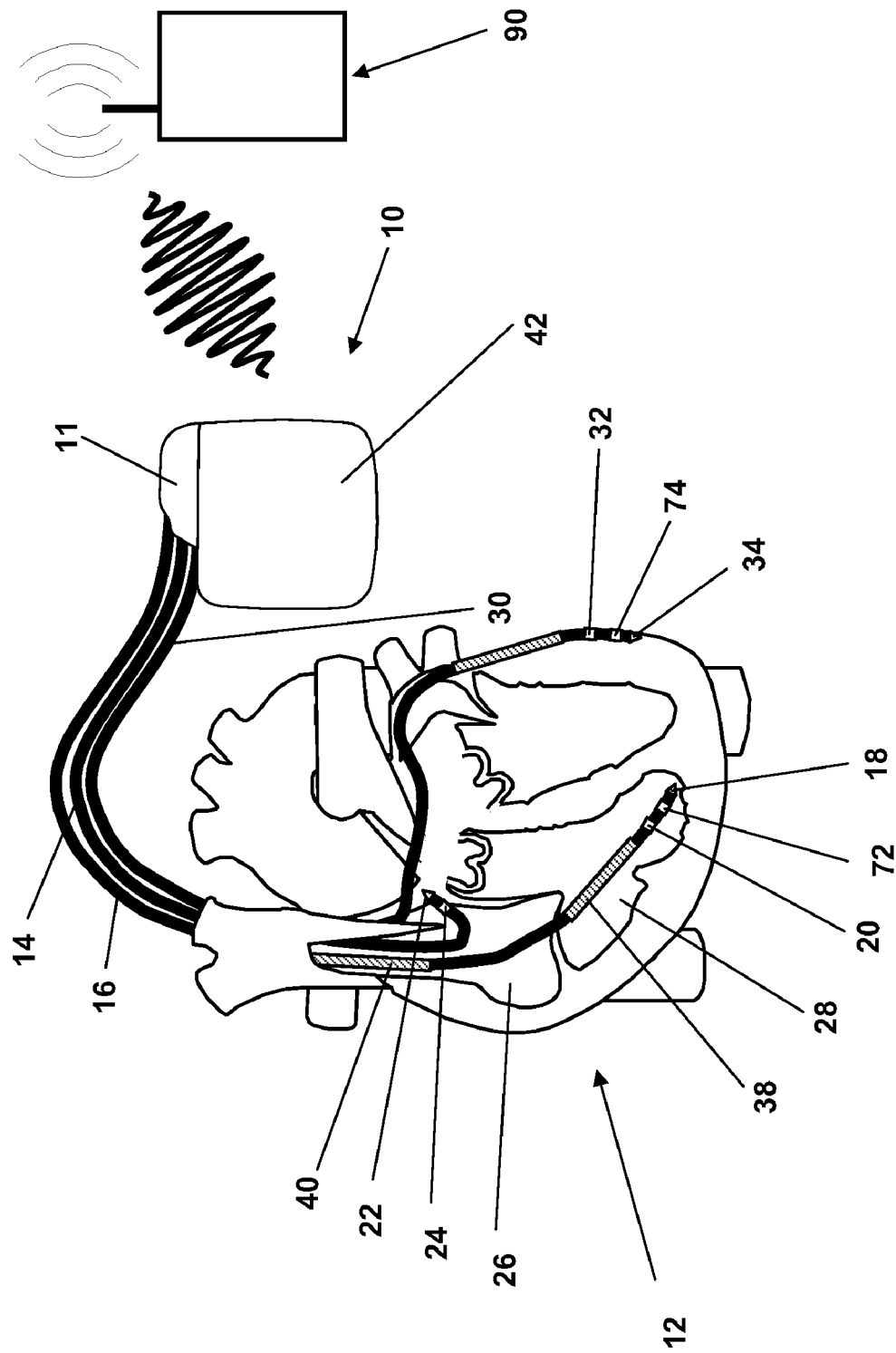
Figure 3:
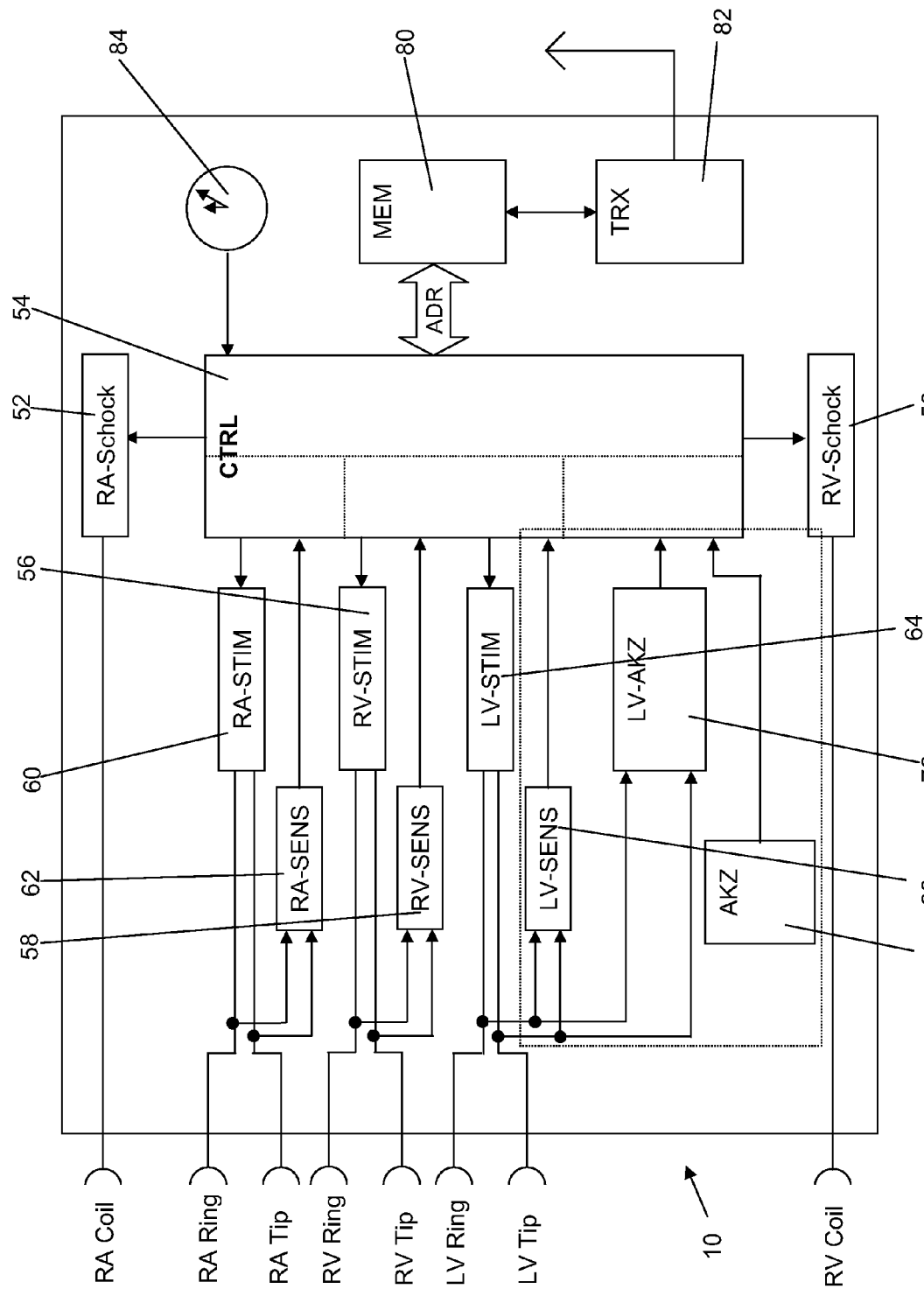
Figure 4:
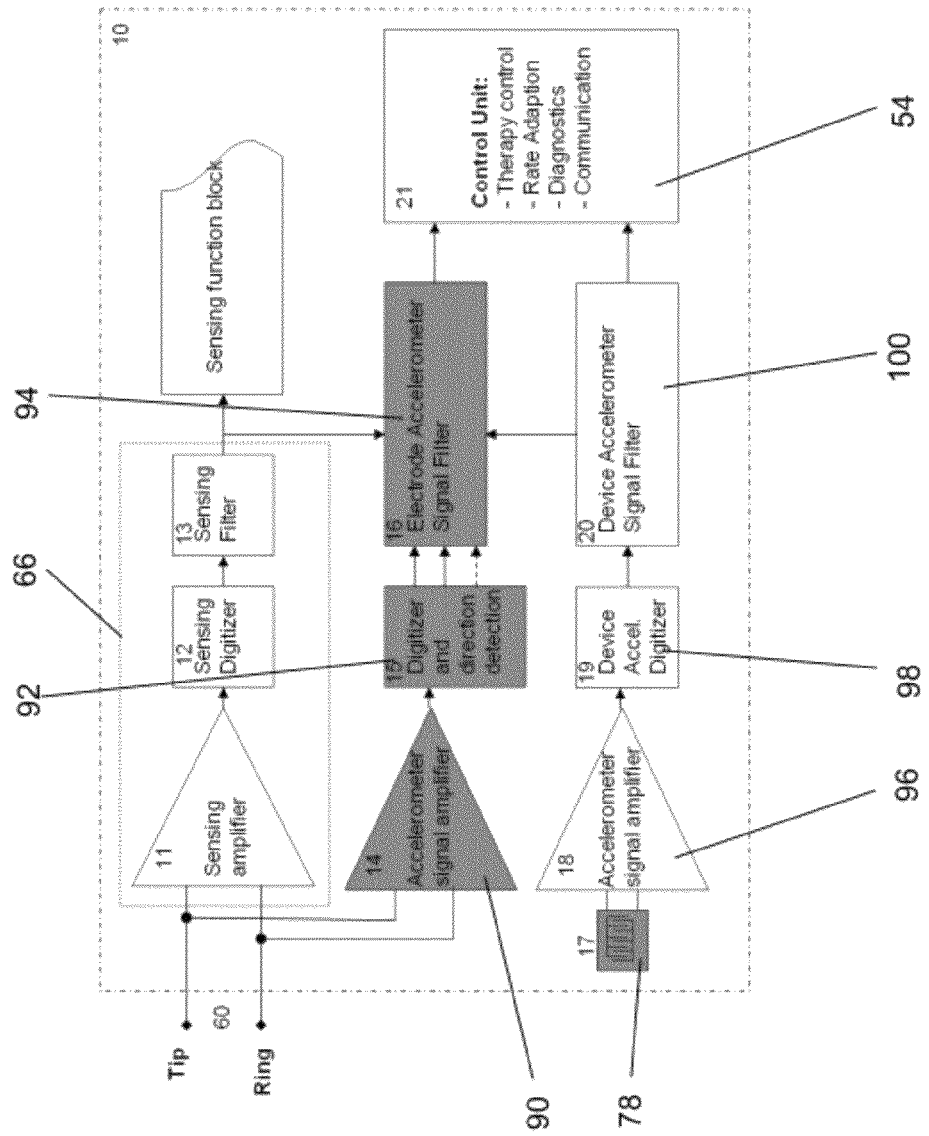
Figure 5:
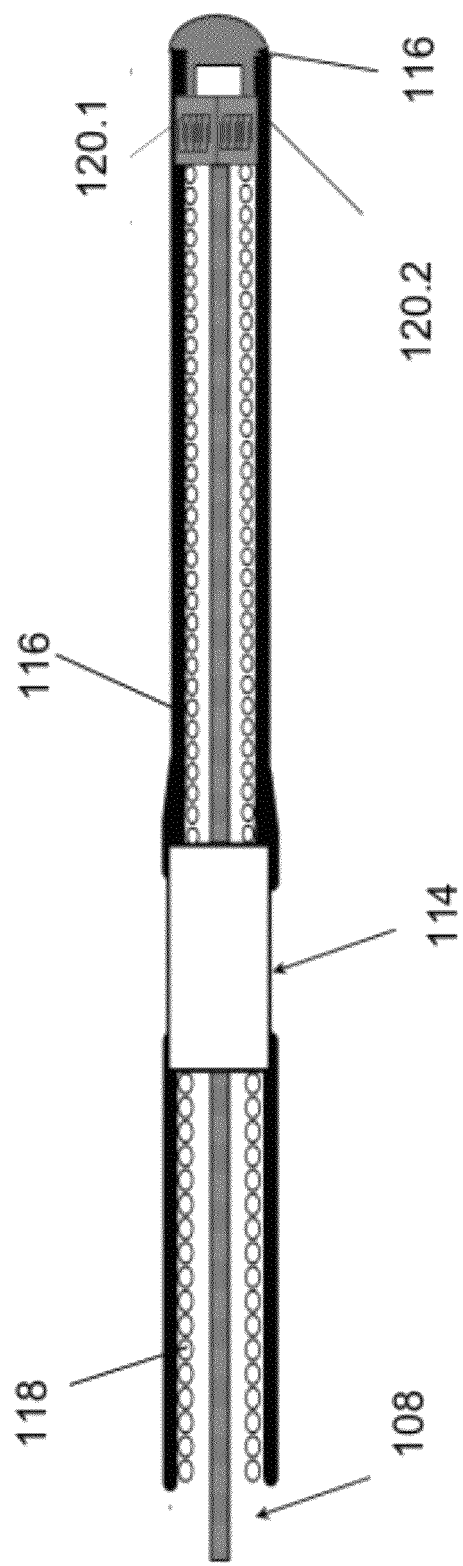
Figure 6:
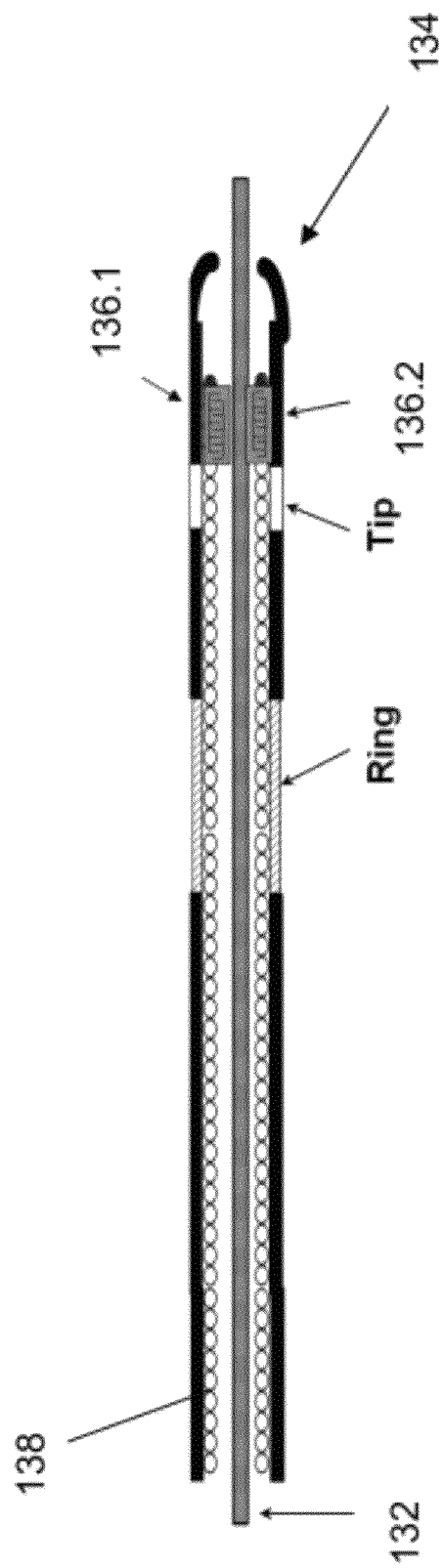

The invention will be explained in greater detail on the basis of an exemplary embodiment with reference to the figures. In the figures:

FIG. 1: shows a schematic illustration of a cardiac therapy system;

FIG. 2: shows an illustration of a cardiac stimulator having connected electrodes situated in the heart;

FIG. 3: shows a schematic block diagram of a cardiac stimulator;

FIG. 4: shows a schematic block diagram for more detailed explanation of the cardiac stimulator according to the invention against the background of the block diagram from FIG. 3;

FIG. 5: shows a longitudinal section through the distal end of an electrode line, to be implanted by stylet, having acceleration sensor; and FIG. 6: shows a longitudinal section through the distal end of an electrode line, to be implanted by stylet, having acceleration sensor.

DETAILED DESCRIPTION OF THE INVENTION

A cardiac therapy system is shown for overview in FIG. 1, which comprises, in addition to an implanted cardiac pacemaker 10, an external device (patient device) 90 and service center 92, symbolically shown by a server. The implantable cardiac stimulator 10 has a telemetry unit, for which it may exchange data wirelessly with the external device 90. The external device 90 is, for example, connected wire-bound to the service center 92, so that overall data may be exchanged between the service center 92 and the implantable cardiac stimulator 10 via the external device 90 as the relay station. A physician team 94 may search the data which the service center 92 has received from the implantable cardiac stimulator 10 via a data-technology access to the service center 92.

FIG. 2 shows the implantable cardiac stimulator 10 in the form of a three-chamber cardiac pacemaker/cardioverter/defibrillator having electrode lines 14, 16, and 30 connected thereto, in connection with a heart 12. In addition, the external device 90 is shown once again in proximity to the implanted cardiac stimulator 10. The electrode lines 14, 16, and 30 are electrically connected via known, standardized plug connections to contact sockets in a header (terminal housing) 11 of the cardiac stimulator 10. In this way, the electrode lines 14, 16, and 30 are also connected to electronic components in the interior of a hermetically sealed metal housing 42 of the cardiac stimulator 10. These components are schematically shown in greater detail hereafter and determine the mode of operation of the cardiac stimulator 10 according to the invention.

The electrode line 14 is a right-atrial electrode line and has an atrial tip electrode RA tip 22 on its distal end and, at a short distance therefrom, an atrial ring electrode RA ring 24, which are both placed in the right atrium 26 of the heart 12.

The electrode line 16 is a right-ventricular electrode line and has a right-ventricular tip electrode RV tip 18 on its distal end and, in direct proximity thereto, a right-ventricular ring electrode RV ring 20. Both electrodes are situated in the apex of the right ventricle 28 of the heart 12.

In addition, the right-ventricular electrode line 16 also has a right-ventricular shock coil RV shock 38 as a large-area electrode for delivering relation shocks. A further shock coil 40 is situated in the superior vena cava and is therefore also referred to hereafter as the SVC shock electrode.

An acceleration sensor 72 is integrated in the right-ventricular electrode line 16 in the area of the distal end of the right-ventricular electrode line 16, which is connected via a modulator (not shown) to an electrical line, which also electrically connects one of the electrodes 18 or 20 to a contact surface of a terminal plug at the proximal end of the right-ventricular electrode line 16.

The electrode line 30 is a left-ventricular electrode line, on whose distal end a left-ventricular tip electrode LV tip 34 is situated, and, in proximity thereto, a left-ventricular ring electrode LV ring 32. In addition, the left-ventricular electrode line 30 carries a left-ventricular shock coil (not identified in greater detail, but shown in FIG. 2) for delivering defibrillation shocks to the left ventricle. The left-ventricular electrode line 30 is led out from the right atrium 26 of the heart 12 via the coronary sinus into a lateral vein branching therefrom and is therefore also referred to as the coronary sinus electrode line or CS electrode line.

An acceleration sensor 74 is also integrated in the left-ventricular electrode line 30, which is also connected via a modulator (not shown) to an electrical line, which also electrically connects one of the electrodes 32 or 34 to a contact surface of a terminal plug at the proximal end of the left-ventricular electrode line 30.

The main components of the cardiac stimulator 10 are shown in FIG. 3. The electrical terminals for the various electrodes 18, 20, 22, 24, 32, 34, 38, and 40 are shown on the left side. The shock electrodes 38 and 40 are each connected to a right-ventricular shock pulse generator 50 or SVC shock generator 52. Both shock generators 50 and 52 are connected to a stimulation control unit 54, which activates the two shock pulse generators 50 and 52 upon demand to generate and deliver a defibrillation shock.

The terminal for the right-ventricular tip electrode RV tip and the terminal for the right-ventricular ring electrode RV ring are each connected to both a right-ventricular stimulation unit 56 and also a right-ventricular sensing unit 58. Both the right-ventricular stimulation unit 56 and also the right-ventricular sensing unit 58 are connected to the stimulation control unit 54.

The right-ventricular stimulation unit 56 is implemented to generate a right-ventricular stimulation pulse upon an activation signal of the stimulation control unit 54 and deliver it via the terminals of the right-ventricular ring electrode RV ring and the right-ventricular tip electrode RV tip. Alternatively, it is also possible that the housing 42 of the cardiac stimulator 10 forms a neutral electrode and the right-ventricular stimulation unit 56 is connected to the terminal for the right-ventricular tip electrode RV tip and the housing 42 as the other electrode to deliver a stimulation pulse. A right-ventricular stimulation pulse differs from a defibrillation shock in that the stimulation pulse has a significantly lower pulse strength, so that it does not excite all of the cardiac tissue (myocardium) of a ventricle at once like a defibrillation shock, but rather only the cardiac muscle cells in the immediate surroundings of the right-ventricular tip electrode RV tip 18. This excitation then propagates further over the entire ventricle by natural stimulation conductance and thus ensures a stimulated contraction of the ventricle.

The right-ventricular sensing unit 58 is implemented to first amplify and filter electrical potentials applied to the terminal for the right-ventricular ring electrode RV ring and the right-ventricular tip electrode RV tip by an input amplifier. Furthermore, the right-ventricular sensing unit 58 is implemented to analyze the curve of the electrical signals applied to its inputs in such a way that the right-ventricular sensing unit 58 independently detects a natural (intrinsic), i.e., independent contraction of the right ventricle. This may occur, for example, in that the curve of the signal applied to the inputs of the right-ventricular sensing unit 58 is compared to a threshold value. The greatest amplitude of the signal in the form of the so-called R wave is typically characteristic for a natural contraction of the right ventricle, which may be detected by threshold value comparison. The right-ventricular sensing unit 58 then outputs a corresponding output signal indicating a natural contraction of the right ventricle to the stimulation control unit 54.

The terminal for the right-atrial tip electrode RA tip and the terminal for the right-atrial ring electrode RA ring are connected in a similar way to a right-atrial stimulation unit 60 and also to a right-atrial sensing unit 62, which are each in turn connected to the stimulation control unit 54. The right-atrial stimulation unit 60 is implemented to generate stimulation pulses whose strength is sufficient to excite the right-atrial myocardium. The right-atrial stimulation pulses may have a different pulse strength than the right-ventricular stimulation pulses. The right-atrial sensing unit 62 is implemented to detect a so-called P wave from the curve of the differential signal applied to its inputs, which characterizes a natural (intrinsic) contraction of the right atrium. If the right-atrial sensing unit 62 detects a corresponding P wave, it generates an output signal, which characterizes a natural contraction of the right atrium, and relays it to the stimulation control unit 54.

In the same way, the terminal for the left-ventricular tip electrode LV tip and the terminal for the left-ventricular ring electrode LV range are connected to a left-ventricular stimulation unit 64 and a left-ventricular sensing unit 66. The left-ventricular stimulation unit 64 and the left-ventricular sensing unit 66 are also connected to the stimulation control unit 54. Both function similarly to the stimulation units 56 and 60 and sensing units 58 and 62 already described.

In addition, the terminals for the left-ventricular tip electrode LV tip and the left-ventricular ring electrode LV ring are connected to a left-ventricular accelerometer analysis unit LV-AKZ 76. The left-ventricular accelerometer analysis unit 76 is implemented to amplify and modulate the modulated accelerometer output signal of the left-ventricular acceleration sensor 74 with the aid of the modulator integrated in the left-ventricular electrode line 30 and finally analyze it. The left-ventricular accelerometer analysis unit 76 finally generates an output signal which is fed to the control unit CTRL 54 for further analysis. The accelerometer output signal fed back in this way is direction-dependent, i.e., the dimension of the output signal is a function of the direction in which an acceleration force acts on the acceleration sensor 74. The acceleration sensor 74 is implemented to generate two accelerometer output signals, which each represent acceleration values for two different directions.

In a similar way as for the left-ventricular acceleration sensor 74, a right-ventricular accelerometer analysis unit may also be provided to be able to analyze output signals of the right-ventricular acceleration sensor 72. However, this is not shown in FIG. 3.

As a further component of the cardiac stimulator 10, a further acceleration sensor 78 is connected to the stimulation control unit 54 and integrated in the housing 42 of the cardiac stimulator 10. The acceleration sensor 78 is implemented to detect a movement signal as a function of the physical activity of a patient and output a corresponding first accelerometer output signal, which indicates the physical activity of the patient, to the stimulation control unit 54. This allows it, upon the analysis of the accelerometer output signals of the right-ventricular acceleration sensor 72 and the left-ventricular acceleration sensor 74, to compensate for the movement of the patient superimposed on the intrinsic cardiac movement by analysis of the signals of the additional acceleration sensor 78 integrated in the housing of the electronic implant.

Furthermore, the cardiac stimulator 10 comprises a storage unit 80, which is connected to the stimulation control unit 54 and allows it to store signals generated or analyzed by the stimulation control unit 54. On the other hand, the storage unit 80 allows it to store control programs for the stimulation control unit 54 in changeable form. The storage unit 80 is used in the context of the present invention in particular for the purpose of storing comparison curves (reference curves) for the analysis of the accelerometer output signals of the acceleration sensors. These comparison curves are recorded with the aid of echocardiography under predefined conditions (e.g., rest) and subsequently stored in the storage unit 80.

Furthermore, the stimulation control unit 54 is connected to a timer 84.

The storage unit 80 is connected to a telemetry unit 82, which allows it to transmit data stored in the storage unit 80 wirelessly to the external device 100 or to transmit programming commands on the part of the external device 100 to the cardiac stimulator 10 and store them in the storage unit 80.

As a three-chamber cardiac stimulator/cardioverter/defibrillator, the cardiac stimulator 10 is capable of performing a stimulation of the right atrium, the right ventricle, and the left ventricle, or also only one or two of these heart chambers in a way known per se. This particularly includes the stimulation of a particular ventricle in the demand mode, in which stimulation pulses are only delivered to the particular ventricle if no intrinsic contraction of the particular ventricle is detected in a preceding particular escape interval on the part of the particular sensing unit. The cardiac stimulator is thus capable of performing the known right-ventricular stimulation modes such as VVI, VVD, or DDD.

For the timing of the stimulation pulses in the biventricular stimulation mode, in which both ventricles of a heart are stimulated, in particular an interventricular delay time (VV interval) is significant, i.e., the time with which a right stimulation pulse and a less stimulation pulse follow one another (if they are not inhibited in the demand mode). This time may be greater than 0, so that the left stimulation pulse follows the right stimulation pulse. The interventricular delay time may be 0, which means that a right-ventricular stimulation pulse and a left-ventricular stimulation pulse are delivered simultaneously by simultaneous activation of the right-ventricular stimulation unit 56 and the left-ventricular stimulation unit 64 by the stimulation control unit 54. The interventricular delay time may also be less than 0, which means that a left-ventricular stimulation pulse is delivered before the delivery of the associated right-ventricular stimulation pulse.

FIG. 4 shows the components of a channel, in this case the left-ventricular channel, which is indicated in FIG. 3 by a dotted line and comprises both a left-ventricular sensing unit 66 and also the left-ventricular accelerometer analysis unit 76, in a more detailed illustration. In regard to the left-ventricular sensing unit 66, it may be seen from FIG. 4 that it comprises an input amplifier 80, an analog-digital converter 82, and finally a digital filter 86, whose output value is fed to a sensing function block of the control unit 54.

In regard to the accelerometer analysis unit 76, it may be seen from FIG. 4 that it also comprises a signal amplifier 90, whose output signal is fed to an analog-digital converter and demodulator 92. The analog-digital converter and demodulator 92 is implemented in particular to reclaim a demodulated signal from the modulated accelerometer output signal received via the electrode line and in particular to obtain two different output signals for two different acceleration directions by demodulation. The output signal of the analog-digital converter and demodulator unit 92 is fed to an accelerometer signal filter 94 and digitally filtered thereby. The output signal of a sensing filter of the sense unit 66 is also fed to the accelerometer signal filter 94. Furthermore, the accelerometer signal filter 94 is connected to the accelerometer 72 integrated in the housing 42 of the cardiac stimulator 10, via a second accelerometer signal amplifier 96, an analog-digital converter 98 connected thereto, and a second accelerometer signal filter 100.

FIG. 5 shows a distal end of a typical electrode line to be implanted with the aid of a stylet. This line has a tip electrode on the far right side of the figure and a ring electrode 114. A liquid-tight envelope 116 seals the electrode line 110 in relation to the surroundings. A wire coil 118 is situated inside the envelope 116, which provides the electrode line 110 with mechanical stability and is simultaneously used as an electrical supply line. A double acceleration sensor 120 (i.e., 120.1 and 120.2 as illustrated) is integrated directly adjoining the tip electrode 112 in the electrode line 110, which has two acceleration pickups 120.1 and 120.2, which record acceleration values in different directions. These acceleration pickups 120.1 and 120.2 are electrically connected via a modulator (not shown) to the wire coil 118 of the electrode line 110 and in this way may modulate an output signal of the acceleration sensor 120 and transmit it to a contact (not shown) of an electrode line plug via the wire coil 118.

FIG. 6 shows a longitudinal section through the distal end of an alternative electrode line. This differs from the electrode line 110 in that it is implantable with the aid of a guide wire 132 and has an open distal end 134 for this purpose. An acceleration sensor 136 having two acceleration pickups 136.1 and 136.2, which each deliver acceleration values for different acceleration directions, is again situated in the area of this open distal end 134. These two acceleration pickups 136.1 and 136.2 are also connected via a modulator (not shown) to a wire coil 138 in the interior of the electrode line 130.

LIST OF REFERENCE NUMERALS

| Reference numeral | Meaning |
|---|---|
| 10 | cardiac stimulator |
| 11 | header (terminal housing) |
| 12 | heart |
| 14 | right-atrial electrode line |
| 16 | right-ventricular electrode line |
| 18 | right-ventricular tip electrode RV tip |
| 20 | right-ventricular ring electrode RV ring |
| 22 | atrial tip electrode RA tip |
| 24 | atrial ring electrode RA ring |
| 26 | right atrium |
| 28 | right ventricle |
| 30 | left-ventricular electrode line |
| 32 | left-ventricular ring electrode LV ring |
| 34 | left-ventricular tip electrode LV tip |
| 38 | right-ventricular shock coil RV shock |
| 40 | shock coil |
| 42 | housing |
| 50 | right-ventricular shock pulse generator |
| 52 | svc shock pulse generator |
| 54 | stimulation control unit |
| 56 | right-ventricular stimulation unit |
| 58 | right-ventricular sensing unit |
| 60 | right-atrial stimulation unit |
| 62 | right-atrial sensing unit |
| 64 | left-ventricular stimulation unit |
| 66 | left-ventricular sensing unit |
| 72 | right-ventricular acceleration sensor |
| 74 | left-ventricular acceleration sensor |
| 76 | accelerometer analysis unit |
| 78 | acceleration sensor integrated in the housing |
| 80 | storage unit |
| 82 | telemetry unit |
| 84 | timer |
| 86 | external device |
| 88 | service center |
| 89 | physician team |
| 90 | signal amplifier |
| 92 | demodulator |
| 94 | accelerometer signal filter |
| 96 | accelerometer signal amplifier |
| 98 | analog-digital converter |
| 100 | second accelerometer signal filter |
| 108 | stylet |
| 110 | stylet-implantable electrode line (distal end) |
| 112 | tip electrode |
| 114 | ring elektrode |
| 116 | envelope |
| 118 | wire coil |
| 120 | acceleration sensor |
| 130 | over-the-wire electrode line (distal end) |
| 132 | guide wire |
| 134 | open distal end |
| 136 | acceleration sensor |
| 138 | wire coil |

What is claimed is:

1. A cardiac stimulation configuration having:
an electrode line comprising
an electrical conductor;
a proximal end, which is implemented to connect the electrode line to an implantable medical device;
a distal end, which comprises
at least one electrode coupled with said electrical conductor and implemented to deliver stimulation pulses or record intracardial electrical signals, and
an acceleration sensor, wherein the acceleration sensor is implemented to record and differentiate acceleration values in at least two different directions;
a radioopaque or echogenic section associated with said distal end;
an implantable cardiac stimulator having
a housing;
a further acceleration sensor that is integrated in the housing of the implantable cardiac stimulator and wherein the further acceleration sensor is implemented to record and differentiate acceleration values in said at least two different directions and wherein said further acceleration sensor is configured to detect movement associated with physical activity of a patient;
an analysis unit, which is at least indirectly connected to the acceleration sensor and the further acceleration sensor wherein said analysis unit is configured to
analyze output signals from said acceleration sensor in relation to said output signals from said further acceleration sensor to compensate for said movement associated with said physical activity of said patient in which said electrode line is implanted to determine distance between said acceleration sensor and said further acceleration sensor that is independent of said physical activity of said patient;
correlate said output signals from said acceleration sensor in said electrode line to hemodynamic findings obtained from a stress/echocardiography test on said patient that utilizes said radioopaque or echogenic section associated with said distal end of said electrode line to calibrate said output signals.

2. The electrode line according to claim 1, further comprising:
a plug contact on the proximal end and an electrical line, which electrically connects a contact surface of the plug contact to the at least one electrode,
wherein the acceleration sensor is connected to a modulator, and wherein the modulator is connected to the electrical line, and wherein the modulator is implemented to provide an output signal of the acceleration sensor in modulated form to the electrical line.

3. The electrode line according to claim 1, wherein the acceleration sensor is connected to a transmitter for wireless transmission of output signals of the acceleration sensor.

4. The electrode line according to claim 1, wherein the electrode line is implemented for implantation through a coronary sinus.

5. The cardiac stimulation configuration according to claim 1 wherein said analysis unit is further implemented to analyze a particular accelerometer output signal by a comparison to reference curves stored in the cardiac stimulator, wherein the stored reference curves have been obtained under defined conditions.

6. The cardiac stimulation configuration of claim 1 further comprising at least one additional electrode line and wherein said electrode line is configured as a left-ventricular electrode line and said at least one additional electrode line is configured as a right-ventricular electrode line.

7. The cardiac stimulation configuration of claim 1 further comprising a modulator coupled with said electrode line and also coupled with said accelerometer wherein said accelerometer outputs acceleration values in said at least two different directions on said electrode line through said modulator.

8. A cardiac stimulation configuration having:
an electrode line comprising an electrical conductor;
a proximal end, which is implemented to connect the electrode line to an implantable medical device;
a distal end, which comprises
at least one electrode coupled with said electrical conductor and implemented to deliver stimulation pulses or record intracardial electrical signals, and
an acceleration sensor, wherein the acceleration sensor is implemented to record and differentiate acceleration values in at least two different directions;
an implantable cardiac stimulator having
a housing;
a further acceleration sensor that is integrated in the housing of the implantable cardiac stimulator and wherein the further acceleration sensor is implemented to record and differentiate acceleration values in said at least two different directions and wherein said further acceleration sensor is configured to detect movement associated with physical activity of a patient;
an analysis unit, which is at least indirectly connected to the acceleration sensor and the further acceleration sensor wherein said analysis unit is configured to analyze output signals from said acceleration sensor in relation to said output signals from said further acceleration sensor to compensate for said movement associated with said physical activity of said patient in which said electrode line is implanted to determine distance between said acceleration sensor and said further acceleration sensor that is independent of said physical activity of said patient.

9. The cardiac stimulation configuration according to claim 8 wherein said analysis unit is further implemented to analyze a particular accelerometer output signal by a comparison to reference curves stored in the cardiac stimulator, wherein the stored reference curves have been obtained under defined conditions.

10. The cardiac stimulation configuration of claim 8 further comprising at least one additional electrode line and wherein said electrode line is configured as a left-ventricular electrode line and said at least one additional electrode line is configured as a right-ventricular electrode line.

11. The cardiac stimulation configuration of claim 8 further comprising a modulator coupled with said electrode line and also coupled with said accelerometer wherein said accelerometer outputs acceleration values in said at least two different directions on said electrode line through said modulator.

* * * * *